US009662434B2

(12) United States Patent
Agarwal et al.

(10) Patent No.: US 9,662,434 B2
(45) Date of Patent: May 30, 2017

(54) BLOWER INSTRUMENT, APPARATUS AND METHODS OF USING

(75) Inventors: Amit Agarwal, San Francisco, CA (US); Michael C. Stewart, San Jose, CA (US); Albert K. Chin, Palo Alto, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 884 days.

(21) Appl. No.: 13/581,291

(22) PCT Filed: Feb. 28, 2011

(86) PCT No.: PCT/US2011/026490
§ 371 (c)(1),
(2), (4) Date: Dec. 13, 2012

(87) PCT Pub. No.: WO2011/106777
PCT Pub. Date: Sep. 1, 2011

(65) Prior Publication Data
US 2014/0018748 A1     Jan. 16, 2014

Related U.S. Application Data

(63) Continuation-in-part of application No. 12/714,037, filed on Feb. 26, 2010, now Pat. No. 9,022,998.

(51) Int. Cl.
*A61M 5/00* (2006.01)
*A61M 3/02* (2006.01)
(Continued)

(52) U.S. Cl.
CPC .......... *A61M 3/0279* (2013.01); *A61B 17/02* (2013.01); *A61M 3/027* (2013.01);
(Continued)

(58) Field of Classification Search
CPC ..... A61B 2017/0243; A61B 2217/007; A61M 3/027; A61M 3/0279
(Continued)

(56) References Cited

U.S. PATENT DOCUMENTS

| 452,131 A | 5/1891 | Haughawout |
|---|---|---|
| 810,675 A | 1/1906 | Richter |

(Continued)

FOREIGN PATENT DOCUMENTS

| DE | 90 04513 | 6/1990 |
|---|---|---|
| EP | 0 293 760 A2 | 12/1988 |

(Continued)

OTHER PUBLICATIONS

Partial Supplementary European Search Report dated Feb. 12, 2015, issued for corresponding EP Patent Application No. 11748232.3, 6 pages.

(Continued)

*Primary Examiner* — Phillip Gray

(57) ABSTRACT

A surgical blower for providing a directed stream to clear a surgical site, that can be used in multiple different use modes. In one use mode, the surgical blower is handheld by a user during operation. In another mode, a distal end portion of the blower is fixed to a foot of a stabilizer instrument and the handle of the blower is handheld. In another mode, a distal end portion of the blower is fixed to a foot of a stabilizer instrument and the handle of the blower is fixed to a stationary object such as a sternal retractor. In another mode, the distal end of the blower is free and the handle of the blower is fixed to a stationary object. An apparatus including a blower and a stabilizer is provided. Methods of using the blower as well as the apparatus are also provided.

20 Claims, 8 Drawing Sheets

(51) Int. Cl.
  *A61B 17/02* (2006.01)
  *A61B 17/00* (2006.01)
  *A61B 17/30* (2006.01)
(52) U.S. Cl.
  CPC ............ *A61B 2017/00477* (2013.01); *A61B 2017/0243* (2013.01); *A61B 2017/306* (2013.01); *A61B 2217/007* (2013.01)
(58) Field of Classification Search
  USPC ................................................ 604/257, 315
  See application file for complete search history.

(56) References Cited

U.S. PATENT DOCUMENTS

| | | |
|---|---|---|
| 1,202,698 A | 10/1916 | Ford |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,392,722 A | 7/1968 | Jorgensen |
| 3,683,926 A | 8/1972 | Suzuki |
| 3,720,433 A | 3/1973 | Rosfelder |
| 3,783,873 A | 1/1974 | Jacobs |
| 3,858,578 A | 1/1975 | Milo |
| 3,858,926 A | 1/1975 | Ottenhues |
| 3,882,855 A | 5/1975 | Schulte et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A * | 9/1977 | Kletschka .......... A61B 17/2812 604/27 |
| 4,052,980 A | 10/1977 | Grams et al. |
| 4,108,178 A | 8/1978 | Betush |
| 4,226,228 A | 10/1980 | Shin et al. |
| 4,230,119 A | 10/1980 | Blum |
| 4,306,561 A | 12/1981 | de Medinaceli |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,673,161 A | 6/1987 | Flynn et al. |
| 4,688,570 A | 8/1987 | Kramer et al. |
| 4,702,230 A | 10/1987 | Pelta |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,829,985 A | 5/1989 | Couetil |
| 4,852,552 A | 8/1989 | Chaux |
| 4,854,318 A | 8/1989 | Solem et al. |
| 4,863,133 A | 9/1989 | Bonnell |
| 4,865,019 A | 9/1989 | Phillips |
| 4,869,457 A | 9/1989 | Ewerlof |
| 4,884,559 A | 12/1989 | Collins |
| 4,892,526 A | 1/1990 | Reese |
| 4,925,443 A | 5/1990 | Heilman et al. |
| 4,941,872 A | 7/1990 | Felix et al. |
| 4,949,707 A | 8/1990 | LeVahn et al. |
| 4,955,896 A | 9/1990 | Freeman |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,131,905 A | 7/1992 | Grooters |
| 5,133,724 A | 7/1992 | Wilson, Jr. et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,203,769 A | 4/1993 | Clement et al. |
| 5,231,974 A | 8/1993 | Giglio et al. |
| 5,242,386 A | 9/1993 | Holzer |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,170 A | 8/1994 | Salermo et al. |
| 5,336,252 A | 8/1994 | Cohen |
| 5,382,756 A | 1/1995 | Dagan |
| 5,383,840 A | 1/1995 | Heilman et al. |
| 5,417,709 A | 5/1995 | Slater |
| 5,437,651 A | 8/1995 | Todd et al. |
| 5,452,733 A | 9/1995 | Sterman et al. |
| 5,467,763 A | 11/1995 | McMahon et al. |
| 5,489,280 A | 2/1996 | Russell |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,529,571 A | 6/1996 | Daniel |
| 5,547,458 A | 8/1996 | Ortiz et al. |
| 5,569,274 A | 10/1996 | Rapacki et al. |
| 5,571,215 A | 11/1996 | Sterman et al. |
| 5,573,496 A | 11/1996 | McPherson et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,772,583 A | 6/1998 | Wright et al. |
| 5,782,746 A | 7/1998 | Wright |
| 5,795,291 A | 8/1998 | Koros et al. |
| 5,799,661 A | 9/1998 | Boyd et al. |
| 5,807,243 A | 9/1998 | Vierra et al. |
| 5,813,410 A | 9/1998 | Levin |
| 5,820,373 A | 10/1998 | Okano et al. |
| 5,830,214 A | 11/1998 | Flom et al. |
| 5,836,311 A | 11/1998 | Borst et al. |
| 5,846,187 A | 12/1998 | Wells et al. |
| 5,846,193 A | 12/1998 | Wright |
| 5,846,194 A | 12/1998 | Wasson et al. |
| 5,846,219 A | 12/1998 | Vancaillie |
| 5,865,730 A | 2/1999 | Fox et al. |
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |

(56) References Cited

U.S. PATENT DOCUMENTS

| | | |
|---|---|---|
| 5,894,843 A | 4/1999 | Benetti et al. |
| 5,899,425 A | 5/1999 | Corey, Jr. et al. |
| 5,906,607 A | 5/1999 | Taylor et al. |
| 5,908,382 A | 6/1999 | Koros et al. |
| 5,927,284 A | 7/1999 | Borst et al. |
| 5,944,658 A | 8/1999 | Koros et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,967,972 A | 10/1999 | Santilli et al. |
| 5,967,973 A | 10/1999 | Sherts et al. |
| 5,976,080 A | 11/1999 | Farascioni |
| 5,976,171 A | 11/1999 | Taylor |
| 5,984,865 A | 11/1999 | Farley et al. |
| 5,984,867 A | 11/1999 | Deckman et al. |
| 6,007,486 A | 12/1999 | Hunt et al. |
| 6,007,523 A | 12/1999 | Mangosong |
| 6,013,027 A | 1/2000 | Khan et al. |
| 6,015,378 A | 1/2000 | Borst et al. |
| 6,017,304 A | 1/2000 | Vierra et al. |
| 6,019,722 A | 2/2000 | Spence et al. |
| 6,027,476 A | 2/2000 | Sterman et al. |
| 6,030,340 A | 2/2000 | Maffei et al. |
| D421,803 S | 3/2000 | Koros et al. |
| 6,032,672 A | 3/2000 | Taylor |
| 6,033,362 A | 3/2000 | Cohn |
| 6,036,641 A | 3/2000 | Taylor et al. |
| 6,050,266 A | 4/2000 | Benetti et al. |
| 6,063,021 A | 5/2000 | Hossain et al. |
| 6,071,295 A | 6/2000 | Takahashi |
| 6,099,468 A | 8/2000 | Santilli et al. |
| 6,102,853 A | 8/2000 | Scirica et al. |
| 6,102,854 A | 8/2000 | Carfier et al. |
| 6,120,436 A | 9/2000 | Anderson et al. |
| 6,139,492 A | 10/2000 | Vierra et al. |
| 6,168,577 B1 | 1/2001 | Niederjohn et al. |
| 6,190,311 B1 | 2/2001 | Glines et al. |
| 6,193,652 B1 | 2/2001 | Berky et al. |
| 6,200,263 B1 | 3/2001 | Person |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,231,506 B1 | 5/2001 | Hu et al. |
| 6,251,065 B1 | 6/2001 | Kochamba et al. |
| 6,283,912 B1 | 9/2001 | Hu et al. |
| 6,290,644 B1 | 9/2001 | Green, II et al. |
| 6,315,717 B1 | 11/2001 | Benetti et al. |
| 6,331,158 B1 | 12/2001 | Hu et al. |
| 6,348,036 B1 | 2/2002 | Looney et al. |
| 6,350,229 B1 | 2/2002 | Borst et al. |
| 6,361,493 B1 | 3/2002 | Spence et al. |
| 6,364,833 B1 * | 4/2002 | Valerio ............ A61B 17/0206 600/205 |
| 6,371,906 B1 | 4/2002 | Borst et al. |
| 6,375,611 B1 | 4/2002 | Voss et al. |
| 6,390,976 B1 | 5/2002 | Spence et al. |
| 6,475,142 B1 | 11/2002 | Parsons et al. |
| 6,506,149 B2 | 1/2003 | Peng et al. |
| 6,558,314 B1 | 5/2003 | Adelman et al. |
| 6,565,508 B2 | 5/2003 | Scirica et al. |
| 6,602,183 B1 | 8/2003 | Levi et al. |
| 6,607,479 B1 | 8/2003 | Kochamba et al. |
| 6,626,830 B1 | 9/2003 | Califiore et al. |
| 6,641,604 B1 | 11/2003 | Adelman et al. |
| 6,656,113 B2 | 12/2003 | Green, II et al. |
| 6,676,597 B2 | 1/2004 | Guenst et al. |
| 6,685,632 B1 | 2/2004 | Hu et al. |
| 6,701,930 B2 | 3/2004 | Benetti et al. |
| 6,730,020 B2 | 5/2004 | Peng et al. |
| 6,733,445 B2 | 5/2004 | Sherts et al. |
| 6,743,169 B1 | 6/2004 | Taylor et al. |
| 6,758,808 B2 | 7/2004 | Paul et al. |
| 6,804,866 B2 | 10/2004 | Lemke et al. |
| 6,849,044 B1 | 2/2005 | Voss et al. |
| 6,890,292 B2 | 5/2005 | Kochamba et al. |
| 6,893,391 B2 | 5/2005 | Taylor |
| 6,899,670 B2 | 5/2005 | Peng et al. |
| 6,902,523 B2 | 6/2005 | Kochamba et al. |
| 6,936,002 B2 | 8/2005 | Kochamba et al. |
| 6,969,349 B1 | 11/2005 | Spence et al. |
| 6,994,669 B1 | 2/2006 | Gannoe et al. |
| 7,018,328 B2 | 3/2006 | Mager et al. |
| 7,056,287 B2 | 6/2006 | Taylor et al. |
| 7,137,949 B2 | 11/2006 | Scirica et al. |
| 7,179,224 B2 | 2/2007 | Willis et al. |
| 7,195,591 B2 | 3/2007 | Spence et al. |
| 7,226,409 B2 | 6/2007 | Peng et al. |
| 7,326,173 B2 | 2/2008 | Guenst et al. |
| 7,338,434 B1 | 3/2008 | Haarstad et al. |
| 7,377,895 B2 | 5/2008 | Spence et al. |
| 7,404,792 B2 | 7/2008 | Spence et al. |
| 7,438,680 B2 | 10/2008 | Guenst et al. |
| 7,497,823 B2 | 3/2009 | Parihar et al. |
| 7,621,911 B2 | 11/2009 | Ariola, Jr. |
| 7,736,307 B2 | 6/2010 | Hu et al. |
| 8,162,817 B2 | 4/2012 | Spence et al. |
| 8,277,476 B2 | 10/2012 | Taylor et al. |
| 8,317,695 B2 | 11/2012 | Spence et al. |
| 2002/0016527 A1 | 2/2002 | Hancock |
| 2004/0030223 A1 | 2/2004 | Calafiore et al. |
| 2007/0066958 A1 | 3/2007 | Wright |
| 2007/0179344 A1 | 8/2007 | Spence et al. |
| 2007/0255272 A1 | 11/2007 | Ariola |
| 2008/0139879 A1 | 6/2008 | Olson et al. |
| 2009/0299131 A1 | 12/2009 | Green, II et al. |
| 2010/0210916 A1 | 8/2010 | Hu et al. |
| 2012/0078061 A1 | 3/2012 | Calafiore et al. |
| 2012/0157788 A1 | 6/2012 | Serowski et al. |

FOREIGN PATENT DOCUMENTS

| | | |
|---|---|---|
| EP | 0 293 760 A3 | 12/1988 |
| EP | 0 293 760 B1 | 12/1988 |
| EP | 0 630 629 | 5/1994 |
| EP | 668 058 A1 | 8/1995 |
| EP | 0 993 806 A2 | 4/2000 |
| FR | 473451 | 1/2015 |
| GB | 168216 | 9/1921 |
| GB | 2 233 561 A | 1/1991 |
| GB | 2 267 827 A | 12/1993 |
| WO | WO 87/04081 | 7/1987 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

Maquet Axius TM Blower/Mister Instructions for Use, Maquet Cardiovascular LLC, 1999.

(56) References Cited

OTHER PUBLICATIONS

Clampless Beating Heart Surgery, Maquet Cardiovascular LLC, internet publication, http://www.maquet.com/content/MAQUET-CardiacSurgery/Documents/Brochures/CBH_BROCHU_FAMILYBROCH_EN_US.pdf, Apr. 2008.

International Search Report and Written Opinion, PCT/US11/26490, Apr. 19, 2011.

Westaby, S. et al., "Less Invasive Coronary Surgery: Consensus From the Oxford Meeting," The Annals of Thoracic Surgery, 62:924-31, 1996.

Zumbro, et al., A A Prospective Evaluation of the Pulsatile Assist Device, The Annals of Thoracic Surgery, vol. 28, No. 2, Aug. 1979, pp. 269-273.

Akins, et al., A Preservation of Interventricular Septal Function in Patients Having Coronary Artery Bypass Graft Without Cardiopulmonary Bypass, @ American Heart Journal, vol. 107, No. 2, Feb. 1984, pp. 304-309.

Ancalmo, N. and J. L. Ochsner: "A Modified Sternal Retractor," Ann. Thorac, Surg. 21 (1976) 174.

Angelini, G.D., M.D. et al., "Fiber-Optic Retractor for Harvesting the Internal Mammary Artery," Ann. Thorac. Surg. (1990; 50:314-5).

Angelini, G.D., M.D., A Simple, Inexpensive Method of Heart Retraction During Coronary Artery Bypass Surgery, Ann. Thora. Surg 46:46-247, Aug. 1988.

Anstadt, M.D., et al., A Direct Mechanical Ventricular Actuation for Cardiac Arrest in Humans, @ Chest, vol. 100, No. 1, Jul. 1991.

Antinori, C. et al., A A Method of Retraction During Reoperative Coronary Operations Using the Favaloro Retractor, @ The Society of Thoracic Surgeons: 1989.

Archer, DO, et al., A Coronary Artery Revascularization Without Cardiopulmonary Bypass, @ Texas Heart Institute Journal, vol. 11, No. 1, Mar. 1984, pp. 52-57.

Arom, K.V., et al., "Mini-Sternotomy for Coronary Artery Bypass Grafting," The Annals of Thoracic Surgery 1996; 61:1271-2.

Ballantyne, M.D., et al., A Delayed Recovery of Severally >Stunned= Myocardium with the Support of a Left Ventricular Assist Device After Coronary Artery Bypass Graft Surgery, @ Journal of the American College of Cardiology, vol. 10, No. 3, Sep. 1987, pp. 710-712.

Bedellino, M.M., et al., "The Cardiac Rag—Simple Exposure of the Heart," Texas Heart Institute Journal, vol. 15, No. 2, 1988, 134-35.

Beg, R.A., et al., "Internal Mammary Retractor," Ann Thorac, Surg., vol. 39, No. 1, pp. 286-287, Jan. 1985.

Benetti, et al., A Direct Coronary Surgery with Saphenous Vein Bypass Without Either Cardiopulmonary Bypass or Cardiac Arrest, @ The Journal of Cardiovascular Surgery, vol. 26, No. 3, May-Jun. 1985, pp. 217-222.

Benetti, et al., A Direct Myocardial Revascularization Without Extracorporeal Circulation, @ Chest, vol. 100, No. 2 Aug. 1991, pp. 312-316.

Bonatti, J., et al., "A Single Coronary Artery Bypass Grafting—A Comparison Between Minimally Invasive Off Pump Techniques and Conventional Procedures," European Journal of Cardio-Thoracic Surgery, 14 (Supp. I) (1998) S7-S12.

Borst, et al., A Coronary Artery Bypass Grafting Without Cardiopulmonary Bypass and Without Interruption of Native Coronary Flow Using a Novel Anastomosis Site Restraining Device (A Octopus @), @ J Am Coll Cardiol, May 1996, vol. 27, No. 6, pp. 1356-1364.

Borst, et al., A Regional Cardiac Wall Immunobilization for Open Chest and Closed Chest Coronary Artery Bypass Grafting on the Beating Heart; >Octopus = Method, @ Circulation, Oct. 15, 1995, vol. 92, No. 8, supplement 1, 1-177.

British Heart Journal, "Coronary Surgery Without Cardiopulmonary Bypass," pp. 203-205, 1995.

Buffolo, et al., A Direct Myocardial Revascularization Without Cardiopulmonary Bypass, @ Thoac. Cardiovasc. Surgeon, 33 (1985) pp. 26-29.

Bugge, M., "A New Internal Mammary Artery Retractor," Thorac. Cardiovasc Surgeon 38, pp. 316-317 (1990).

Calafiore, A. M., et al., "Minimally Invasive Coronary Artery Bypass Grafting," The Annals of Thoracic Surgery, 62:1545-8, 1996.

Campalani et al., "A New Self-Retaining Internal mammary Artery Retractor." J. Cardiovas. Surg., vol. 28. (1987).

Cartier, R, MD., "Triple Coronary Artery Revascularization on the Stabilized Beating Heart: Initial Experience," Montreal Heart Institute, CJS, vol. 41, No. 4, pp. 283-288, Aug. 1998.

Chaux, A. and C. Blanche, "A New Concept in Sternal Retraction: Applications for Internal Mammary Artery Dissection and Valve Replacement Surgery," Ann. Thorac. Surg. 42, pp. 473-474, Oct. 1986.

Cooley, D. A., "Limited Access Myocardial Revascularization," Texas Heart Institute Journal, pp. 81-84, vol. 23, No. 2, 1996.

Correspondence and Brief Communications, Archives of Surgery—vol. 115, 1136-37, Sep. 1980.

Cremer, J, MD, "Off-Bypass Coronary Bypass Grafting Via Minithoracotomy Using Mechanical Epicardial Stabilization," The Annals of Thoracic Surgery, 63:S79-83, 1997.

DelRossi, A J and Lemole, GM, "A New Retractor to Aid in Coronary Artery Surgery," The Annals of Thoracic Surgery, vol. 36, No. 1, 101-102, Jul. 1983.

Fanning, MD., A Reoperative Coronary Artery Bypass Grafting Without Cardiopulmonary Bypass, @ The Annals of Thoracic Surgery, vol. 55, No. 2, Feb. 1993, pp. 486-489.

Favaloro, M.D., et al, A Direct Myocardial Revascularization by Saphenous Vein Graft, @ The Annals of Thoracic Surgery, vol. 10, No. 2, Aug. 1970.

Fonger, et al., A Enhanced Preservation of Acutely Ischemic Myocardium with Transeptal Left Ventricular Assist, @ The Annals of Thoracic Surgery, vol. 57, No. 3, Mar. 1994, pp. 570-575.

Gacioch, et al., A Cardiogenic Shock Complicating Acute Myocardial Infarction: The Use of Coronary Angioplasty and the Integracion of the New Support Device into Patient Management, @ Journal of the American College of Cardiology, vol. 19, No. 3, Mar. 1, 1992.

Green, GE., "Technique of Internal Mammary-Coronary Artery Anastomosis," The Journal of Cardiovascular Surgery, 78:455-79, 1979.

Groopman, J., "Heart Surgery, Unplugged; Making the Coronary Bypass Safer, Cheaper, and Easier," The New Yorker, Jan. 11, 1999, pp. 43-46, 50-51.

Guzman, F. M.D., "Transient Radial Nerve Injury Related to the Use of a Self Retraining Retractor for Internal Mammary Artery Dissection," J. Cardiovasc. Surg. 30, 1989, pp. 1015-1016.

Hasan, RI, et al., "Technique of Dissecting the Internal Mammary After Using the Moussalli Bar," European Journal of Cardiothoracic Surgery, 4:571-572, 1990.

Itoh, Toshiaki, M.D., et al., "New Modification of a Mammary Artery Retractor," Ann. Thorac. Surg. 9, 1994; 57:1670-1.

Izzat, FRCS, et al., A Cardiac Stabilizer for Minimally Invasive Direct Coronary Artery Bypass, @ Elsevier Science Inc., 1997 by the Society of Thoracic Surgeons.

Japanese Journal of Thoracic Surgery, vol. 42, No. 2, 1989.

Kazama, S. et al., "Fabric Heart Retractor for Coronary Artery Bypass Operations," The Annals of Thoracic Surgery, 55:1582-3, 1993.

Kolessov, M.D., A Mammary Artery-Coronary Artery Anastomosis as Method of Treatment for Angina Pectoris, @ Thoracic and Cardiovascular Surgery, vol. 54, No. 4, Oct. 1967, pp. 535-544.

Konishi, T. MD, et al., "Hybrid-Type Stabilizer for Off-Pump Direct Coronary Artery Bypass Grafting," Annals of Thoracic Surgery 66:961-2, 1998.

(56) References Cited

OTHER PUBLICATIONS

Kresh, et al., A *Heart-Mechanical Assist Device Interaction*, @ Trans. Am. Soc. Artif. Intern. Organs, vol. XXXII, 1986, pp. 437-443.

Lavergne, et al., "*Transcatheter Radiofrequency Ablation of Atrial Tissue Using a Suction Catheter*," PACE, vol. 12, Jan. 1989, Part II, pp. 177-186.

Lonn, M.D., et al. A *Coronary Artery Operation Supported by the Hemopump: An Experimental Study on Pigs*, @ The Annals of Thoracic Surgery, vol. 58, No. 1, Jul. 1994, pp. 516-523.

Matsuura, A. MD, et al., "*A New Device for Exposing the Circumflex Coronary Artery*," The Annals of Thoracic Surgery, 59:1249-50, 1995, pp. 1249-1250.

McGee, et al. A *Extended Clinical Support with an Implatnable Left Ventricular Assist Device*, @ Trans. Am Soc. Artif. Intern. Organs, vol. XXXV, 1989, pp. 614-616.

McKeown, P.P. et al., "*A Modified Sternal Retractor for Exposure of the Internal Mammary Artery*," Ann. Thorac. Surg. 32 (1981) 619.

Ochsner, JL, et al., "*Surgical Management of Diseased Intracavitary Coronary Arteries*," The Annals of Thoracic Surgery, vol. 38, No. 4, July, pp. 356-362, Oct. 1984.

Parsonnet, V. MD, et al., "*Graduated probes for Coronary Bypass Surgery*," The Journal of Thoracic and Cardiovascular Surgery, vol. 68, No. 3, 424-26 (Sep. 1974).

Parsonnet, V. MD, et al., "*Self-Retaining Epicardial Retractor for Aortocoronary Bypass Surgery*," The Journal of Thoracic and Cardiovascular Surgery, 629-30 1979.

Perrault, L. et al., "*Snaring of the Target Vessel in Less Invasive Bypass Operations Does Not Cause Endothelial Dysfunction*," The Society of Thoracic Surgeons, pp. 751-755, 1997.

Pfister, et al., A *Coronary Artery Bypass Without Cardiopulmonary Bypass*, @ The Annals of Thoracic Surgery, vol. 54, No. 6, Dec. 1992, pp. 1085-1092.

Phillips, Steven J., M.D. et al., "*A Versatile Retractor for Use in Harvesting the Internal Mammary Artery and Performing Standard Cardiac Operations*," J. Thorac. Cardiovasc. Surg. (1989; 97:633-5).

Pittman, John, M.D., et al., "*Improved Visualization of the Internal Mammary Artery with a New Retractor System*," Ann. Thorac. Surg., 1989; 48:869-70.

Riahi, et al., A *A Simple Technique and Device to Provide a Bloodless Operative Field in Coronary Artery Surgery Without Cross-Clamping the Aorta*, @ The Journal of Thoracic and Cardiovascular Surgery, vol. 66, No. 6., Dec. 1973, pp. 974-978.

Robicsek, F., "*Aortic Spoon-Jaw Clamp for Aorta-Saphenous Vein Anastomosis*," Journal of Cardiac Surgery, 10:583-585, 1995.

Robinson, et al., A *A Minimally Invasive Surgical Method for Coronary Revascularization—Preliminary Experience in Five Patients*, @ Circulation, Oct. 15, 1995, vol. 92, No. 8, 1-176.

Rousou, J. et al., "*Cardiac Retractor for Coronary Bypass Operations*," The Society of Thoracic Surgeons, pp. 52:877-878, 1991.

Roux, D. MD. et al., "*New Helper Instrument in Cardiac Surgery*," The Annals of Thoracic Surgery, 48: 595-6, 1989.

Roux, D., M.D. et al., "*Internal Mammary Artery Dissection: A Three Dimensional Sternal Retractor*," J. Cardiovasc. Surg., 1989; 30:996-7.

Ruzevich et al. A *Long-Term Follow-up of Survivors of Postcardiotomy Circulatory Support*, @ Trans. Am. Soc. Artif. Intern. Organs, vol. XXXIV, 1988, pp. 116-124.

Scholz, et al. A *Transfemoral Placement of the Left Ventricular Assist Device >Hemopump= During Mechanical Resuscitation*, @ Thoracic and Cardiovascular Surgeon, vol. 38 (1990) pp. 69-72.

Trapp and R. Bisarya, A *To Use or Not to Use the Pump Oxygenator in Coronary Bypass Operations*, @ The Annals of Thoracic Surgery, vol. 19, No. 1, Jan. 1975, pp. 108-109.

Trapp, et al., "*Placement of Coronary Artery Bypass Graft without Pump Oxygenator*," Journal of the Society of Thoracic Surgeons and The Southern Thoracic Surgeons Assn. vol. 19, No. 1, Jan. 1975.

Vigano, M., "*Tecnica Operatoria*," Minerva Cardioangiologica, vol. 23—N. 6-7 (1975).

Vincent, J.G., "*Compact Single Post Internal Mammary Artery Dissection Retractor*," Eur. J. Cardio-Thor. Surg. 3 (1989) 276-277.

Burfeind, Jr., et al., High-Flow Gas Insufflation to Facilitate MIDCABG: Effects on Coronary Endothelium. Ann. Thorac Surg, 66:1246-1249, 1998.

Hoerstrup, et al., Improved Visualization in Minimally Invasive coronary Bypass Graffing, Ann. Thorac Surg 1998, 66-936-4, 1998.

Maddaus, et al., Coronary Artery Surgery Without caadiopulmonary Bypass: Usefulness of the Surgical Blower-Humidifer. Journal of Cardiac Surgery, vol. 7:348-350, 1992.

* cited by examiner

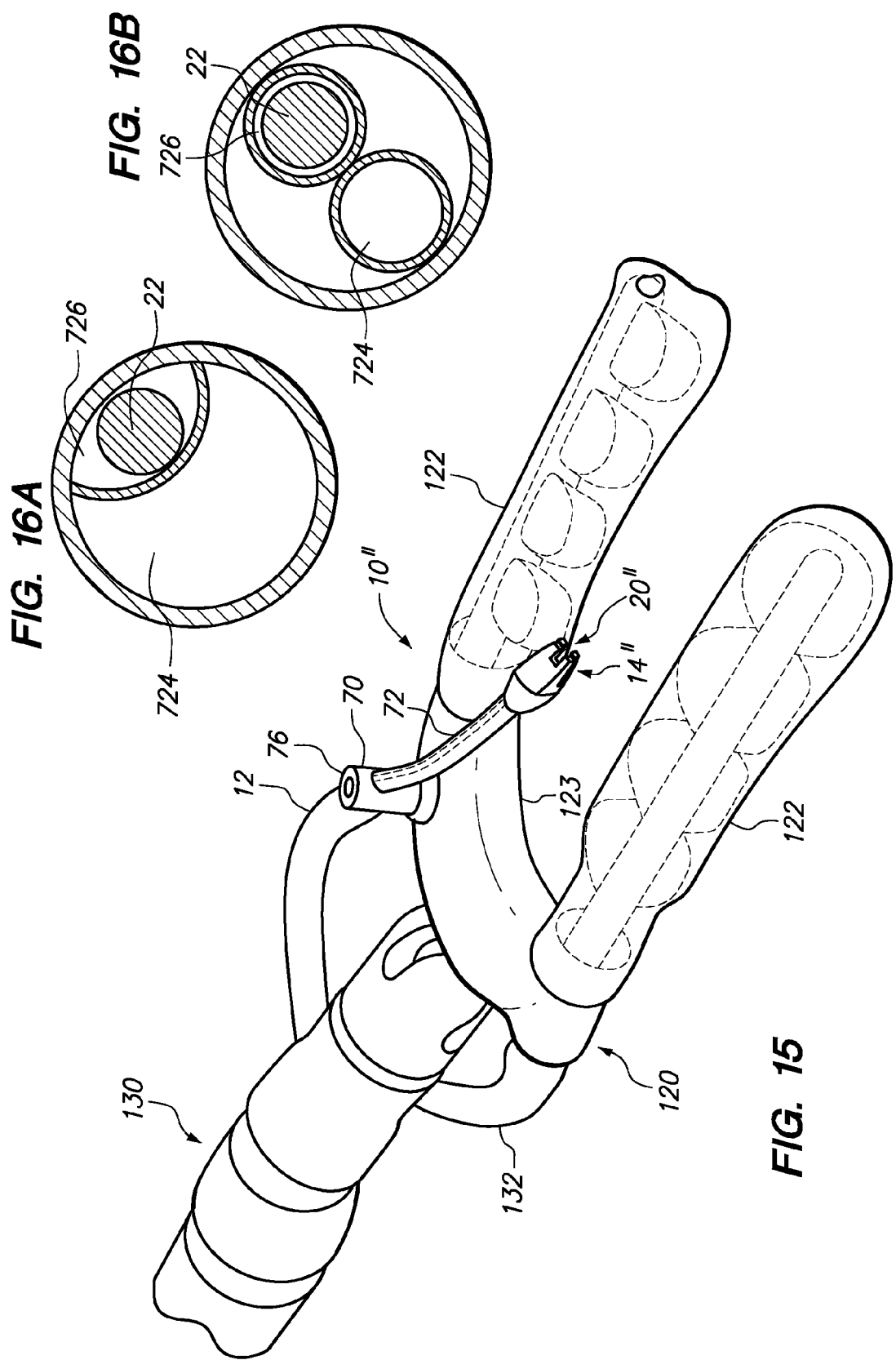

BLOWER INSTRUMENT, APPARATUS AND METHODS OF USING

CROSS REFERENCE TO RELATED APPLICATIONS

This application is a 371 National Stage Application of International Application No. PCT/US11/26490 filed Feb. 28, 2011, which claims the benefit of U.S. application Ser. No. 12/714,037, filed Feb. 26, 2010, the disclosures of which are herein incorporated by reference in their entireties.

FIELD OF THE INVENTION

The present invention relates generally to surgical instruments, and more particularly to a versatile surgical apparatus for providing a directed stream of gas and/or fluid to a surgical site to improve visibility, wherein the apparatus can be used alone or combined with another surgical instrument and/or mounted to a fixed structure.

BACKGROUND OF THE INVENTION

A difficult aspect of many surgical procedures is obtaining and maintaining clear and unobstructed visibility at the surgical site. Accordingly, the instruments and fixtures used in a surgical setting are meticulously designed and selected to ensure that the surgeons have optimum visual access to the surgical site. In most instances, irrigation and suction are used in one form or another to wash away and remove unwanted or undesirable material, fluids, or other particulates. In prolonged surgical procedures, irrigation is also useful in preventing the deleterious effects of tissue desiccation.

Visibility requirements are particularly acute when the surgery involves particularly delicate or small structures, such as those routinely encountered in vascular or neurological surgery. In a vascular anastomosis procedure, for example, even small amounts of fluid or other material can significantly affect the surgeon's view of the anastomotic site. Blood flow from the surrounding tissues or from the vessels themselves is particularly problematic for visualization of the surgical site during an anastomosis. In such procedures, standard liquid irrigation alone is often ineffective for clearing the surgical site.

Instruments using a directed gas or fluid stream to obtain a clear view of the surgical site are known. For example, U.S. Pat. No. 5,336,170 to Salerno et al. discloses a surgical site visualization wand which has a fluid delivery conduit having a fan shaped tip for delivering a pressurized gas to a target site. The visualization wand may also have a humidification or moisturizing conduit for the selective introduction of a sterile liquid in the form of a mist carried by and intermixed with the gas stream to the target site. Such arrangements tend to have the improved ability to blow away fluid or debris without desiccating tissue. U.S. Pat. No. 5,336,170 is hereby incorporated herein in its entirety, by reference thereto. Directed stream visualization instruments such as those described in U.S. Pat. No. 5,336,170 are cumbersome to operate, offering inadequate gas and liquid flow control. If the flow rate of the gas supply is too low, it will not adequately clear the targeted site of undesired material. If the gas stream is delivered at an excessive flow rate or pressure it tends to cause a certain amount of spattering of the cleared material and may displace or damage the delicate tissue structures under operation. If the flow rate of the liquid is too high it may over-irrigate the site; too low and the surrounding tissue may become desiccated.

The directed stream blower disclosed in U.S. Pat. No. 6,168,577 provides a flow controller directly on the handle of the instrument for convenient one-handed operation during use. U.S. Pat. No. 6,168,577 is hereby incorporated herein in its entirety, by reference thereto. The directed stream blower instrument of U.S. Pat. No. 6,168,577 however, like the instrument disclosed in U.S. Pat. No. 6,168,577, is a stand alone instrument that must be individually handheld, independent of other instruments that may be required for the surgical procedure. Typically, a directed stream instrument of this type is held by a surgical assistant, who must then frequently communicate with the surgeon to coordinate position of a blower mister stream, as needed, in the locations needed, at the times needed, and at the flow rates/pressures needed. Additionally, the extra space taken up by the person holding the directed stream instrument and/or the additional space required by the separate instrument itself may be deleterious, especially in instances where the surgical working space is already very limited.

U.S. Pat. No. 6,994,669 discloses a blower that is removably attachable to another surgical instrument at a distal end portion thereof. However, it appears that a proximal end portion of the blower still needs to be held by an operator, which would thereby require an occupation of an additional hand, whether that of the surgeon or a surgeon's assistant. Additionally, the direction of the blower stream does not appear to be adjustable.

U.S. Pat. No. 7,056,287 discloses a blower mounted on a distal end portion of another surgical instrument wherein the blower is adjustable via a malleable tube that includes the lumen through which pressurized gas is delivered. However, this blower is not removable from the additional surgical instrument. Also, bending of the malleable tube can cause kinking, which can adversely affect the flow characteristics of the pressurized gas through the malleable tube.

In view of the foregoing, it would be desirable to provide a blower mister instrument that is more versatile than those of the prior art, that can be used as a standalone instrument, or alternatively can be combined with another instrument, and which may even be used in still further additional operating configurations. It would further be desirable to provide a blower mister instrument that has the capability of changing and controlling a direction in which pressurized fluids are emitted from a distal tip of the instrument, wherein lumens through which the fluids are delivered are formed by conduits that do not readily kink and are not malleable. Still further it would be desirable to provide a blower mister instrument wherein a length from the distal tip to the handle of the instrument is adjustable.

SUMMARY OF THE INVENTION

In one aspect, the present invention provides a surgical blower including an elongated, flexible tube having a lumen extending therethrough; and an attachment member at a distal end portion of the blower, the attachment member being configured and dimensioned for releasable attachment to a mating member of a stabilizer instrument.

In one aspect, the present invention provides a surgical blower instrument for providing a directed stream to clear a surgical site. In at least one embodiment the instrument includes an elongated flexible tube having a first lumen extending therethrough; a malleable shaft extending alongside at least a distal portion of the elongated flexible tube; and a handle, wherein at least a portion of the flexible, elongated tube extends through the handle and the flexible, elongated tube extends distally of the handle.

In at least one embodiment, the elongated flexible tube is a non-malleable tube.

In at least one embodiment, the elongated flexible tube comprises a second lumen, the second lumen being separate and independent of the first lumen.

In at least one embodiment, the tube is a first tube and a second tube is provided with a second lumen, wherein the second tube extends within the first lumen of the first tube.

In at least one embodiment, the elongated, flexible tube comprises a first tube, the blower further comprising a second tube comprising a second elongated, flexible tube, the second tube comprising a second lumen extending therethrough.

In at least one embodiment, the blower comprises a distal tip, wherein the distal ends of the first and second tubes are in fluid communication with the distal tip.

In at least one embodiment, the blower instrument includes a distal tip, wherein the tube is in fluid communication with the distal tip.

In at least one embodiment, the blower instrument includes an attachment member adjacent the distal tip, the attachment member being configured and dimensioned to attach to a mating member on a stabilizer instrument.

In at least one embodiment, the mating member is on a foot of the stabilizer instrument.

In at least one embodiment, the attachment member comprises a post.

In at least one embodiment, a sleeve extends distally from a distal end of the handle, and the elongated, flexible tube and the malleable shaft extend within the sleeve.

In at least one embodiment, at least the elongated, flexible tube is extendible beyond a distal end of the sleeve, to increase a distance between a distal end of the tube and a distal end of the sleeve.

In at least one embodiment, the blower instrument includes a clip configured and dimensioned to attach to a stationary object.

In at least one embodiment, the clip is configured and dimensioned to attach to a sternal retractor.

In at least one embodiment, the clip is longitudinally adjustable relative to the handle, to vary a distance that a distal end of the blower extends beyond the clip.

In at least one embodiment, the blower instrument comprises a flow adjustment mechanism connected to the flexible, elongated tube and adjustable to change a flow property of fluid through the lumen.

In another aspect, the present invention provides an apparatus for use in performing surgical procedures, the apparatus including: a surgical blower instrument for providing a directed stream to clear a surgical site, the blower comprising an elongated flexible tube having a lumen extending therethrough and an engagement member at a distal end portion of the blower; and a stabilizer instrument comprising a shaft; and a foot coupled to a distal end of the shaft, the foot including a mating member; the engagement member being configured and dimensioned for engagement with the mating member.

In at least one embodiment, the engagement member is configured and dimensioned for releasable attachment to the mating member.

In at least one embodiment, the flexible tube is non-malleable.

In at least one embodiment, the foot extends generally along a direction of a longitudinal axis of the foot, wherein the engagement member and the mating member, when attached, maintain a distal tip of the blower at a predefined, non-parallel angle relative the plane along which the contact surface of the contact member generally extends, while allowing rotation of the distal tip about an axis perpendicular to the plane.

In at least one embodiment, the blower further comprises a handle at a proximal end portion thereof, the flexible tube and the engagement member being extendible to increase a distance thereof from the handle.

In at least one embodiment, the foot includes a plurality of the mating members each located at relatively different locations on the foot.

In another aspect, the present invention provides a stabilizer instrument comprising a shaft and a foot coupled to a distal end of the shaft, the foot including a mating member.

In another aspect, the present invention provides a stabilizer instrument for stabilizing a portion of a tissue surface during a surgical procedure, the instrument including: an elongated shaft, a foot coupled to a distal end of the shaft and a connector mechanism at a proximal end portion of the stabilizer instrument, the connector mechanism configured to fix the instrument to a stationary object; the foot including a mating member configured to releasably mate with an attachment member on a distal end portion of a blower instrument, the mating member being configured and dimensioned for releasable attachment to the attachment member.

In at least one embodiment, the foot includes a plurality of the mating members each located at relatively different locations on the foot.

In at least one embodiment, the shaft is flexible in a first, unlocked configuration, and rigid in a second, locked configuration.

In at least one embodiment, the foot extends generally along a direction of a longitudinal axis of the foot, wherein the attachment member and the mating member, when attached, maintain a distal tip of the blower at a non-parallel angle relative to the plane along which the contact surface of the contact member generally extends, while allowing rotation of the distal tip about an axis perpendicular to the plane.

In another aspect, the present invention provides a surgical blower for providing a directed stream to clear a surgical site, wherein the blower includes: an elongated flexible tube having a lumen extending therethrough; a handle, wherein at least a portion of the flexible tube extends through the handle and the flexible tube extends distally and proximally of the handle; a clip configured and dimensioned to attach the blower to a stationary object; and an attachment member at a distal end portion of the blower, the attachment member being configured and dimensioned for releasable attachment to a mating member of another instrument; wherein the flexible tube and the attachment member are extendible to increase a distance thereof from the handle.

In at least one embodiment, the clip is longitudinally adjustable relative to the handle, to vary a distance that a distal end of the blower extends beyond the clip.

In another aspect, the present invention provides a method of facilitating a surgical procedure, the method including: stabilizing a portion of a tissue surface with a stabilizer instrument, wherein the portion includes a surgical target location; attaching a distal end portion of a blower to a foot of the stabilizer instrument; and directing fluid to the surgical target location.

In at least one embodiment, the method further includes attaching a proximal end portion of the blower to a stationary object other than the stabilizer instrument.

In at least one embodiment, the attachment of the proximal end portion includes attaching the proximal end portion to a surgical retractor.

In at least one embodiment, the method includes rotating the distal end portion to redirect a flow of the fluid.

In at least one embodiment, the method further includes detaching the distal end portion from the foot and retracting the distal end portion to reduce a distance between the distal end portion and a proximal end of the blower.

In at least one embodiment, the method includes detaching the proximal end portion and hand holding the proximal end portion.

In at least one embodiment, the method includes detaching the distal end portion from the foot and operating the blower as a handheld instrument.

In at least one embodiment, the method includes retracting the distal end portion to reduce a distance between the distal end portion and a proximal end of the blower.

In another aspect, the present invention provides a method of operating a surgical blower instrument, the method including: fixing a proximal end portion of the blower instrument to a stationary object; adjusting the blower instrument to vary a distance from a distal end of the blower instrument to a location where the blower instrument is fixed to the stationary object; and flowing fluid out of a distal end of the blower instrument.

In at least one embodiment, the adjusting comprises extending a tube out of a distal end of a sheath that the tube passes through.

In at least one embodiment, the adjusting comprises sliding a handle of the instrument relative to a clip used to perform the fixing a proximal end portion.

In another aspect, the present invention provides a stabilizer foot for use in a stabilizer instrument for stabilizing a portion of a tissue surface during a surgical procedure, wherein the foot includes: a contact member having a contact surface adapted to contact the portion of the tissue to be stabilized; and a mating member configured to releasably mate with an attachment member on a distal end portion of a blower instrument, the mating member being configured and dimensioned for releasable attachment to the attachment member.

In at least one embodiment, the foot comprises a fitting adapted to attach to a shaft of the stabilizer instrument.

In another aspect, the present invention provides an assembly for use in a surgical procedure, wherein the assembly includes: a surgical blower tip releasably attached to a stabilizer foot; an attachment member connected to and extending from the surgical blower tip; the stabilizer foot comprising a mating member; the attachment member being releasably attached to the mating member.

In another aspect, the present invention provides an assembly for use in a surgical procedure, wherein the assembly includes: a surgical blower tip releasably attached to a stabilizer foot.

In another aspect, the present invention provides an apparatus for use in performing surgical procedures, wherein the apparatus includes: a stabilizer instrument comprising a foot having a contact member with a contact surface adapted to contact tissue to perform a stabilizing function; and a surgical blower instrument mounted to the stabilizer instrument and configured to provide a directed stream to clear a surgical site, the blower instrument comprising at least one nozzle and the blower instrument being configured for fluid communication with a source of fluid to deliver the fluid out of the at least one nozzle; wherein the blower instrument is user adjustable to change a pattern of spray delivered from the at least one nozzle to a surgical site adjacent the contact member.

In at least one embodiment, the surgical blower instrument comprises a tube, the at least one nozzle formed through a wall thereof.

In at least one embodiment, the tube is rotatable about a longitudinal axis thereof, relative to the contact member.

In at least one embodiment, the tube is axially translatable relative to the contact member.

In at least one embodiment, an actuator is connected to the tube and configured to facilitate movement of the tube by a user of the apparatus.

In at least one embodiment, a hood extends along a length of the contact member, the hood including a slot along a length thereof.

In at least one embodiment, the hood is configured and dimensioned to receive the tube therein, wherein the tube is rotatable with the hood to align the at least one nozzle with the slot thereby allowing delivery of spray through the slot, the tube being further rotatable to position the at least one nozzle out of alignment with the slot thereby preventing delivery of spray through the slot.

In at least one embodiment, the surgical blower instrument is mounted to the stabilizer instrument via a rigid post, the surgical blower instrument comprising a malleable distal portion having the at least one nozzle at a distal end thereof; wherein the malleable distal portion is manipulatable by a user to hold a desired configuration that causes the at least one nozzle to be pointed in a desired direction and orientation.

In at least one embodiment, an actuator is mounted to the shaft in fluid communication with the at least one nozzle, wherein the actuator is operable to prevent spray from flowing through the at least one nozzle in a first configuration, and to allow spray to flow through the at least one nozzle in a second configuration.

These and other features of the invention will become apparent to those persons skilled in the art upon reading the details of the instruments, apparatus, assemblies and methods as more fully described below.

BRIEF DESCRIPTION OF THE DRAWINGS

FIG. 1 is a perspective view of a blower instrument according to an embodiment of the present invention.

FIG. 2A is a cross-sectional view of the instrument of FIG. 1 taken along line 2A-2A.

FIGS. 2B-2C are alternative embodiments of what is shown in FIG. 2A.

FIG. 3 illustrates the malleable nature of the shaft of the blower instrument shown.

FIG. 4 illustrates a bottom view of a handle and clip of a blower instrument according to an embodiment of the present invention.

FIG. 5 schematically illustrates an embodiment of an incremental positioning mechanism according to the present invention.

FIG. 6A illustrates the ability of the distal tip of the blower instrument to be extended distally away from the shaft according to an embodiment of the present invention.

FIG. 6B illustrates a tip/nozzle of the blower instrument according to an embodiment of the present invention.

FIG. 6C illustrates a clip attached to a structure according to an embodiment of the present invention.

FIG. 7 shows an apparatus comprising a blower instrument and a stabilizer instrument according to an embodiment of the present invention.

FIG. 8 schematically illustrates a configuration of attachment member and mating member to maintain a distal tip/nozzle of the blower instrument at a predefined, non-parallel angle relative to the stabilizer foot.

10B shows mating members provided on a stabilizer foot.

Figure 11A:
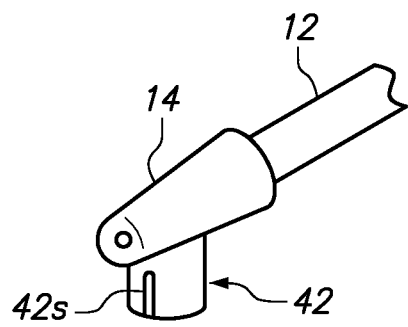
Figure 11B:
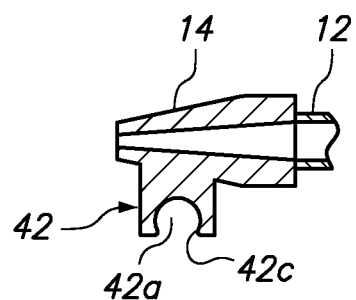

FIGS. 11A-11B show another alternative embodiment of an attachment member provided on a blower device distal tip according to the present invention.

Figure 11C:
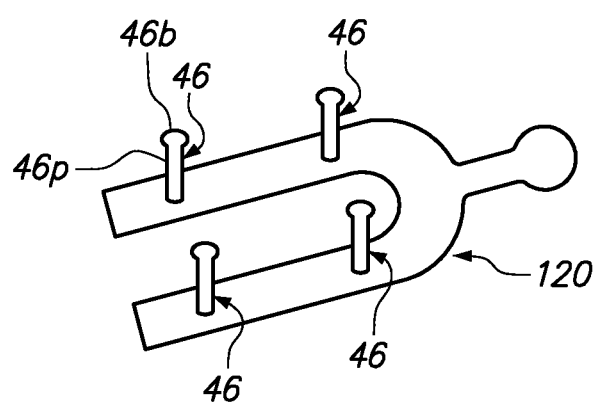

FIG. 11C shows mating members provided on a stabilizer foot.

Figure 12:
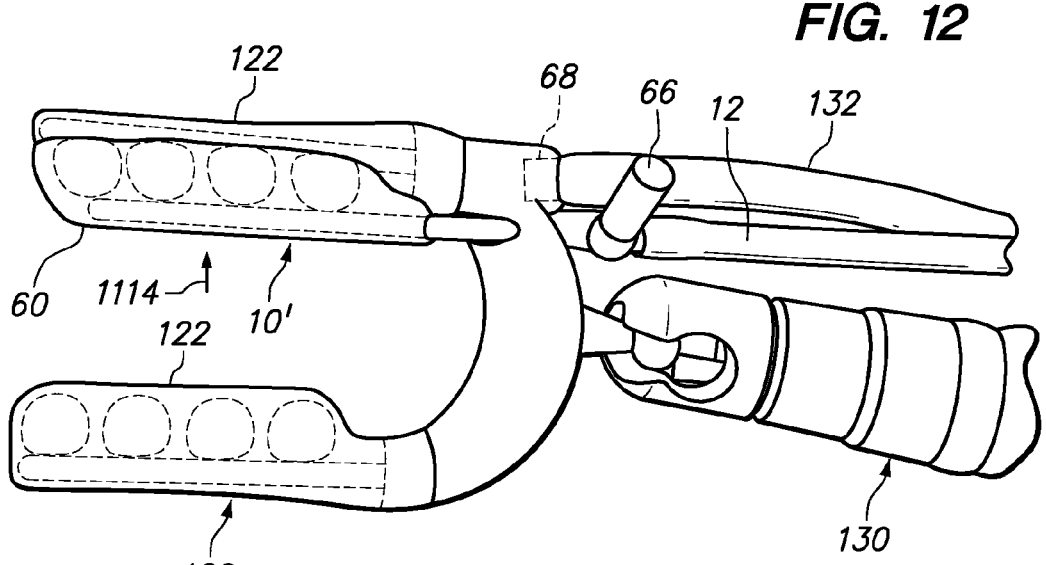

FIG. 12 illustrates a blower instrument mounted to a stabilizer instrument according to another embodiment of the present invention.

Figure 13:
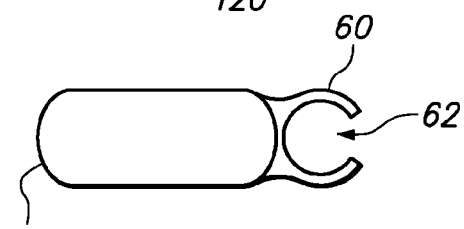

FIG. 13 illustrates an end view of the top contact member shown in FIG. 12.

FIGS. 14A-14D illustrate various configurations of a tube relative to a hood according to an embodiment of the present invention.

FIG. 15 illustrates a blower instrument mounted to a stabilizer instrument according to another embodiment of the present invention.

FIGS. 16A-16B are cross-sectional illustrations showing variations in configurations of lumens within the blower instrument of FIG. 15.

DETAILED DESCRIPTION OF THE INVENTION

Before the present instruments, apparatuses and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a lumen" includes a plurality of such lumens and reference to "the tube" includes reference to one or more tubes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "malleable" as used herein refers to a material property wherein the material plastically deforms under the forces applied thereto for the normal use of the material being described. For example, a tube or conduit that is malleable and is bent by hand, plastically deforms to retain the bent shape after the hand of the person performing the bending no longer contacts the tube or conduit. A "non-malleable" tube or conduit, in contrast, does not maintain the bent shape after the persons hand no longer contacts it, but either elastically returns to its original, pre-bent shape, or at least remains flexible, so that the bent shape is not maintained.

Instruments, Apparatus and Methods

Referring to the drawings in detail wherein like numerals indicate like elements, the present invention includes a blower instrument, which typically provides blower and mister functions and is configured to deliver a stream of pressurized fluid from a distal tip of the instrument. The fluid delivered may be gas or liquid or both, and is typically both, combining a pressurized gas such as carbon dioxide with an atomized liquid such as saline. The blower instrument is useful for removing unwanted materials from a surgical site, thus improving the visibility at the surgical site.

The blower instrument of the present invention is very versatile, in that it may be used in many different modes of use. In at least one embodiment, the blower instrument may be used in a handheld mode where it is handheld by the user and the stream is directed by the user. Another mode of use involves fixing a proximal end portion of the instrument to a stationary object, which may be, but is not limited to an arm of a sternal retractor, and the distal end of the instrument can be manipulated to direct the fluid flow in the desired direction, after which, the user no longer needs to handle the instrument unless and until the direction of the delivered fluid needs to be changed and/or the flow characteristics of the fluid need to be changed. Another mode of use and also other embodiments involve attaching a distal tip of the blower instrument to a foot or crosspiece of a stabilizer instrument. In at least one embodiment, this mode can be used together with fixing the proximal end portion of the blower instrument to a stationary object, or together with holding the proximal end portion of the blower instrument by hand, or the instrument can be simply laid down on a surface without fixing it thereto. In at least one embodiment, one or more openings or nozzles of the instrument may be both rotationally and translationally (axially) adjusted relative to a foot of a stabilizer.

In at least one embodiment, the blower instrument includes an extendible tube that allows the distal tip, where the fluid stream is ejected, to be extended to increase its distance from the handle of the instrument, or retracted, to decrease its distance from the handle.

In at least one embodiment, the blower instrument also includes the capability of controlling the amount of flow of fluid out the distal end thereof. Various flow control mechanisms are described.

A stabilizer instrument is provided that includes a stabilizer foot mounted to a distal end of a shaft or arm. Typically, the stabilizer instrument is provided with a mounting structure at a proximal end portion thereof that is configured to mount the stabilizer instrument to a stationary object such as a sternal retractor. The foot of the stabilizer instrument includes at least one mating member configured to releasably mate with an attachment member on the distal end portion of the blower instrument.

Figure 1:
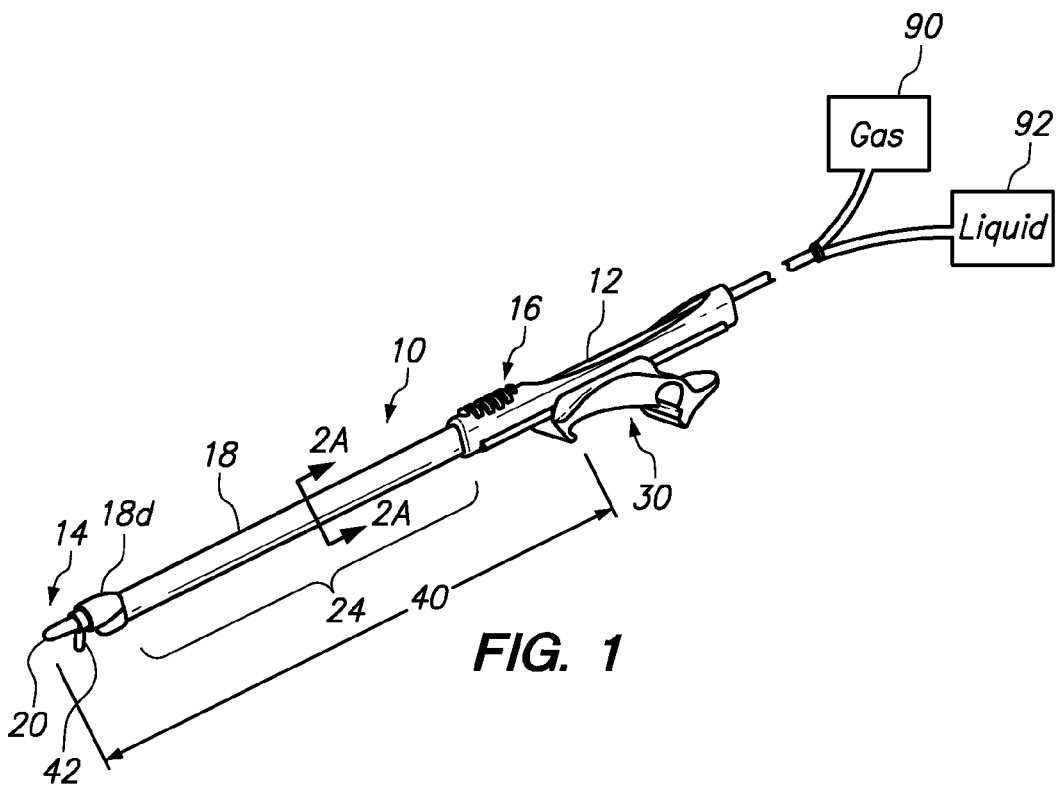

FIG. 1 is a perspective view of a blower instrument 10 according to an embodiment of the present invention. Blower instrument 10 includes an elongated, flexible, non-malleable tube 12 having at least one lumen extending therethrough for delivery of fluid from a fluid source (e.g., pressurized gas source 90 and/or liquid source 92) connected thereto, through the instrument 10 and out of a distal tip 14. One non-limiting example of a gas provided by pressurized gas source 90 is medical grade carbon dioxide. One non-limiting example of a liquid provided by liquid source 92 is sterile saline.

Tube 12 extends through instrument 10 as shown in FIG. 1. Tube 12 extends proximally of handle 16, through handle 16, and distally through flexible sheath 18 to extend at least flush with and typically distally of the distal end of sheath 18. Flexible sheath 18 may be made from flexible polymers, elastomers in mesh or solid sheet configuration, as either a metallic or polymeric spring or combination thereof, etc. Optionally, the distal end of tube 12 may be fixed to a removable nozzle 20 to form the distal tip of instrument 10. If nozzle 20 is not employed, the distal end of tube 12 (or multiple tubes, in other embodiments, as described in more detail below) forms the distal tip of instrument 10. Flexible sheath 18 extends distally of handle 16 to the distal end portion of the instrument 10. Flexible sheath 18 is non-malleable and houses tube 12 (and optionally, an additional tube), as well as malleable rod 22 (e.g., see FIGS. 2A-2C) that runs alongside tube 12. Malleable rod 22 may be made from aluminum, or stainless steel or other material that is malleable when formed in the shape of an elongated rod and is useable in medical instrumentation. Accordingly, the shaft 24 of instrument 10 bounded by sheath 18 is malleable and can be manipulated by hand to bend in any direction or multiple directions, so as to orient the tip 14 of the instrument to direct a stream of fluid toward a desired target, at the appropriate angle, etc.

Figure 2A:
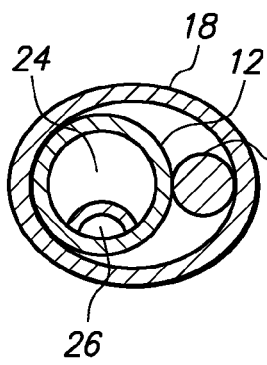

FIG. 2A is a cross-sectional view of instrument 10 of FIG. 1, taken along line 2A-2A. In this embodiment, a single tube 12 is employed that has two lumens 24, 26, one for delivery of the pressurized gas therethrough, and the other for deliver of liquid therethrough. The pressurized gas and liquid are combined at the distal tip 14 of the device 10 so that the liquid is atomized and delivered in a stream together with the pressurized gas.

Figure 2B:
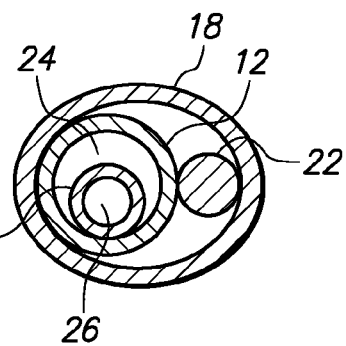
Figure 2C:
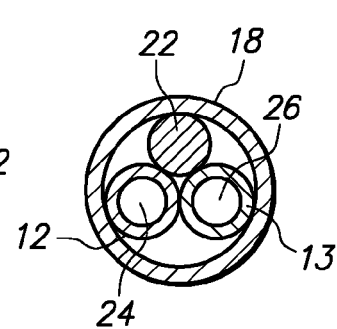

FIG. 2B shows a cross-sectional view of an alternate arrangement in which two tubes 12, 13 are used to form the lumens 24 and 26, respectively. Tube 13 extends through the lumen 24 of tube 12 in this embodiment. Further alternatively, FIG. 2C shows an embodiment in which tubes 12, 13 are provided to run side by side of one another. In either case, tube 13 may be fixed to tube 12, such as by gluing, heat welding, etc., or tubes 12 and 13 may be unfixed along the lengths thereof and joined only at the distal tip 14, either by connection to nozzle 20, or by joining the distal end portions of tube 12 and 13 together without a nozzle.

Malleable rod 22 may be fixed to the inner wall of sheath 18 so that it is prevented from translating relative to sheath 18. Alternatively, malleable rod 22 may be fixed to tube 12 (or to both tubes 12 and 13) and not fixed to sheath 18, so that when tube 12 (or tubes 12, 13) is/are extended beyond the distal end of sheath 18 (as described in further detail below), malleable rod 22 extends with tube 12 (or tubes 12, 13) so that the extended portion of the tube(s) may be held in a desired orientation by manipulation of the malleable rod 22. If rod 22 is fixed to sheath 18, then the extended portion of tube 12 (or tubes 12 and 13) beyond the distal end of sheath 18 is/are flexible and does/do not retain an orientation that it is manipulated to, absent some other form of fixation, since tubes 12 and 13 are non-malleable, typically being made of polyurethane or some other flexible, non-malleable plastic.

Figure 3:
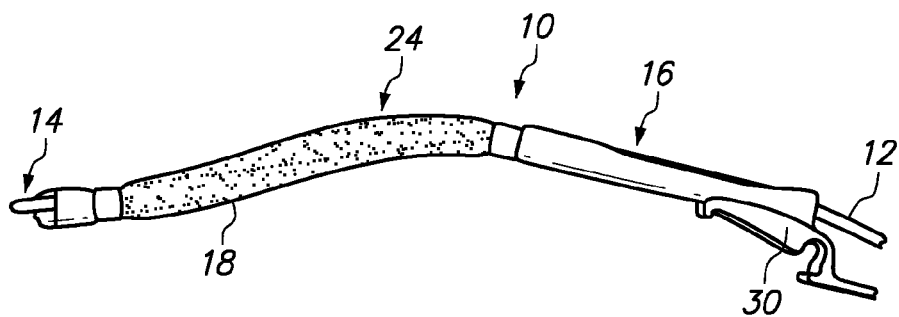

FIG. 3 shows the blower instrument 10 after it has been manipulated to bend the instrument shaft 24. As can be seen, the shaft 24 retains the bent shape even with no external forces applied thereto, due to the malleable nature of rod 22 contained therein. Instrument 10 is additionally provided with a clip 30 slidably configured relative to handle 16. FIG. 3 shows clip 30 slid to its proximal most position relative to handle 16. Clip 30 is configured to be fixed to a stationary object, so that instrument 10 can be mounted to the stationary object so that it need not be handheld during operation. In the embodiment shown and further depicted in FIG. 6C, clip 30 is configured to clip onto a rail 9 of a sternal retractor 8 to fix the instrument to an arm of the sternal retractor. An example of such a rail configuration is shown and described in U.S. Pat. No. 6,283,912, which is hereby incorporated herein, in its entirety, by reference thereto. Alternatively, clip 30 may be configured to readily fix to other stationary objects, such as the crossbar of a surgical retractor or other stationary object.

Figure 4:
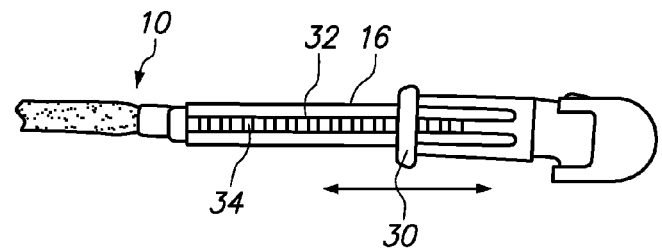
Figure 5:
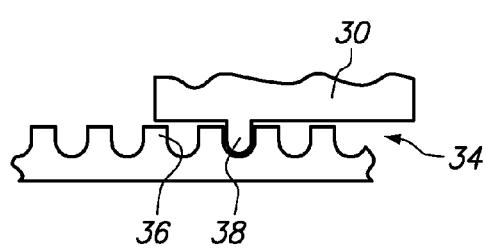

Clip 30 is longitudinally slidable relative (along the directions of the arrows shown in FIG. 4) to handle 16 along a slot 32 or longitudinal rail provided in handle 16, as shown in FIG. 4. Slot 32 may be configured and dimensioned to form a friction fit with clip 30 that can be overcome by manual force, but wherein the clip 30 retains its position relative to handle 16 after release of that force, so that it maintains a desired relative position during use of the instrument 10 fixed to a stationary object. Alternatively, an incremental positioning mechanism 34 may be provided between clip 30 and handle 16 that allows longitudinal movements of clip 30 relative to handle 16, but which retains the relative positions thereof at defined increments along slot 32, wherein the defined increments require more force to bypass than is typically experienced during use of the instrument 10 when it is attached to a stationary object via clip 30. In the example shown in FIG. 4, the incremental positioning mechanism 34 includes a rack of ratchet teeth 36 and clip 30 includes a pawl 38 that rests at positions between the teeth, e.g., see the schematic illustration of FIG. 5. Alternative incremental positioning mechanisms 34 that may be employed include, but are not limited to: a detent mechanism comprising a series of sockets or holes in slot 32 and a retractable ball on clip 30 or a series of retractable balls along slot 32 and a socket or hole in clip 30. By slidably adjusting the position of clip 30 relative to handle 16 in any of the manners described, the user is able to vary the distance 40 (see FIG. 1) that the distal tip 14 extends from clip 30, thus varying the distance that tip 14 extends away from a stationary object that clip 30 is fixed to.

Referring again to FIG. 1, blower instrument 10 is provided with an attachment member 42 proximally adjacent the distal tip 14 (as in FIG. 1) or, alternatively, directly affixed to distal tip 14. Attachment member 42 is configured and dimensioned to attach to a mating member on a stabilizer instrument, described in greater detail below. As shown, attachment member 42 comprises a post that extends outwardly, transverse to the longitudinal axis of the distal tip 14, tube(s) and, optionally nozzle 20. Alternative forms of attachment member 42 may be substituted, together with alternative forms of mating member. For example, attachment member 42 may be a clamp, rod with detent member, etc.

Attachment member 42 may be attached to the mating member on the foot of a stabilizer instrument even while instrument 10 is in the configuration shown in FIG. 1. However, in order to reduce obstruction, provide more working space in the vicinity of the stabilizer foot and/or enable the blower instrument 10 to be fixed to a stationary object or handheld from a further distance or simply laid down on a surface further away from the stabilizer foot, distal tip 14 can be extended distally away from shaft 18 as illustrated in FIG. 6. In the embodiment of FIG. 6, the bends in the portion of the tubing shown extending from the sheath 18 between sheath 18 and distal tip 14 is flexible and this will not hold a preconfigured bend. However, when attachment member 42 is fixed to a stabilizer foot, then the direction of flow through the distal tip 14 can be controlled as described below. Optionally, malleable rod 22 may extend with tube 12 as illustrated by phantom lines in FIG. 6. In this case, the bends shown can be maintained by the malleable property of the rod 22 as it is bent with the tube 12 and thus tip 14 can be used in the configuration shown, without attaching it to a stabilizer foot and with assurance that the orientation of the tip will be maintained by the malleable property of the extended rod 22.

Figure 6B:
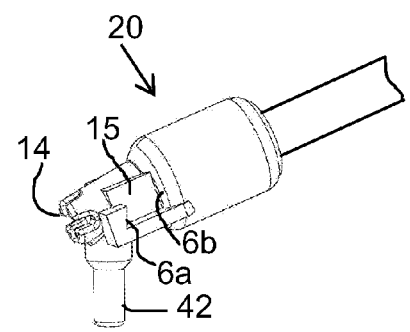
Figure 6A:
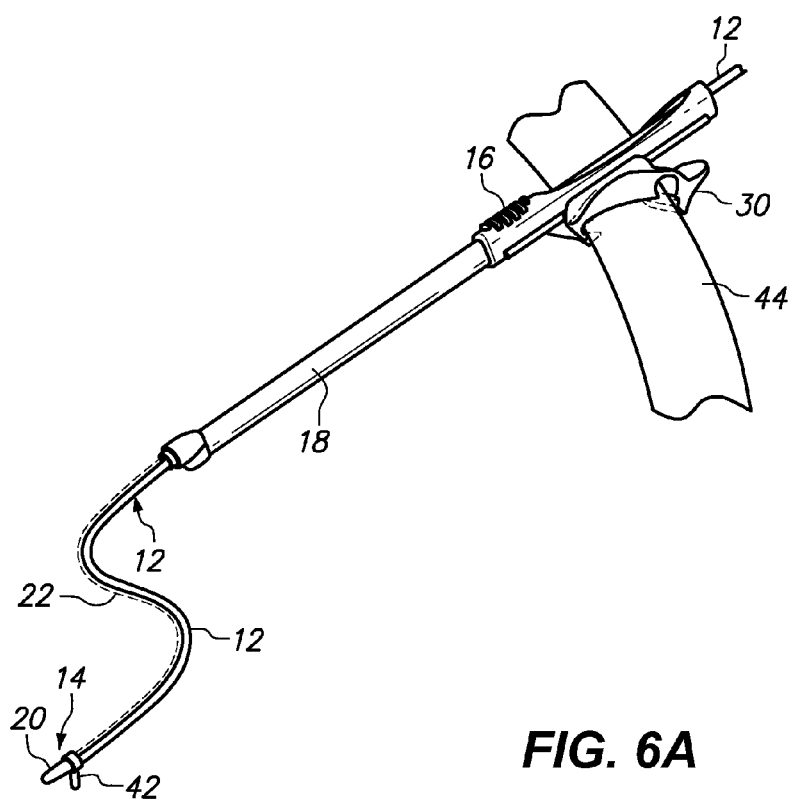

As shown in FIG. 6B, distal tip 14/nozzle 20 may have a recess 15 on each side of the nozzle 20 for a pair of forceps or tweezers to assist in mounting or dismounting distal tip 14/nozzle 20 through the mounting member 42. Preferably the recesses terminate in generally flat surfaces and are parallel to each other in an offset manner. Additionally, the recesses may have a distal surface (facing proximally) and a proximal surface (facing distally) for allowing nozzle 20 to be pulled from and pushed into sheath 18.

Figure 6C:
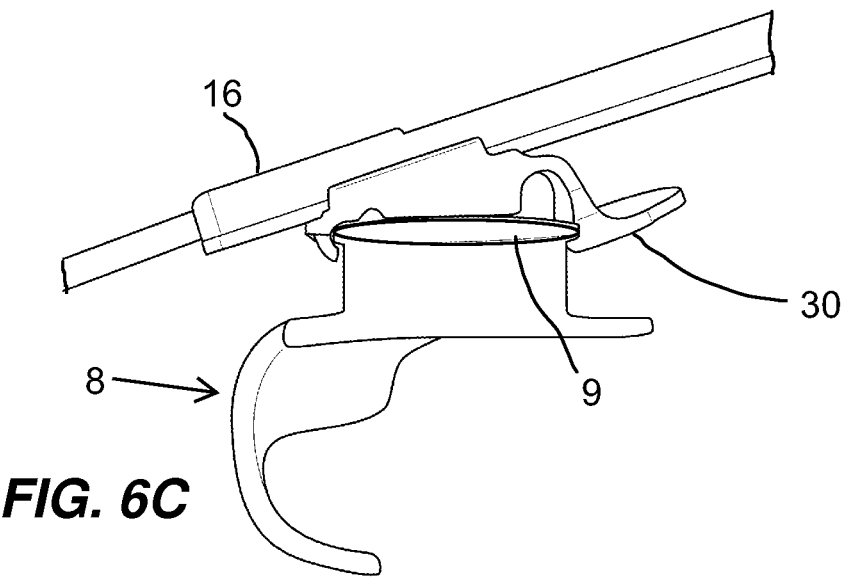

Distal tip 14 can be maintained in the configuration (non-extended configuration) shown in FIG. 1 by forming a friction fit with the distal end 18d of the sheath 18 for example. Alternatively, the friction fit can be replaced by screw threads, bayonet fitting, or numerous other equivalent temporary fixation mechanisms. Also, when the tip is extracted and extends distally from the distal end of the sheath 18 via tubing 12 as shown in FIG. 6, frictional resistance between the tubing and the distal end portion of sheath 18 maintains the tubing 12 in the position it is left in relative to sheath 18, until tubing 12 is pushed back into the sheath 18 or extracted further from the sheath 18. FIG. 6 further illustrates clip 30 fixed to a stationary object 44 (sternal retractor arm, in this instance). FIG. 6C further illustrates clip 30 reversibly fixed to a stationary object 44, wherein the object 44 is a retractor blade 87 and has a rail 88 for clip 30 to attach to.

Figure 7:
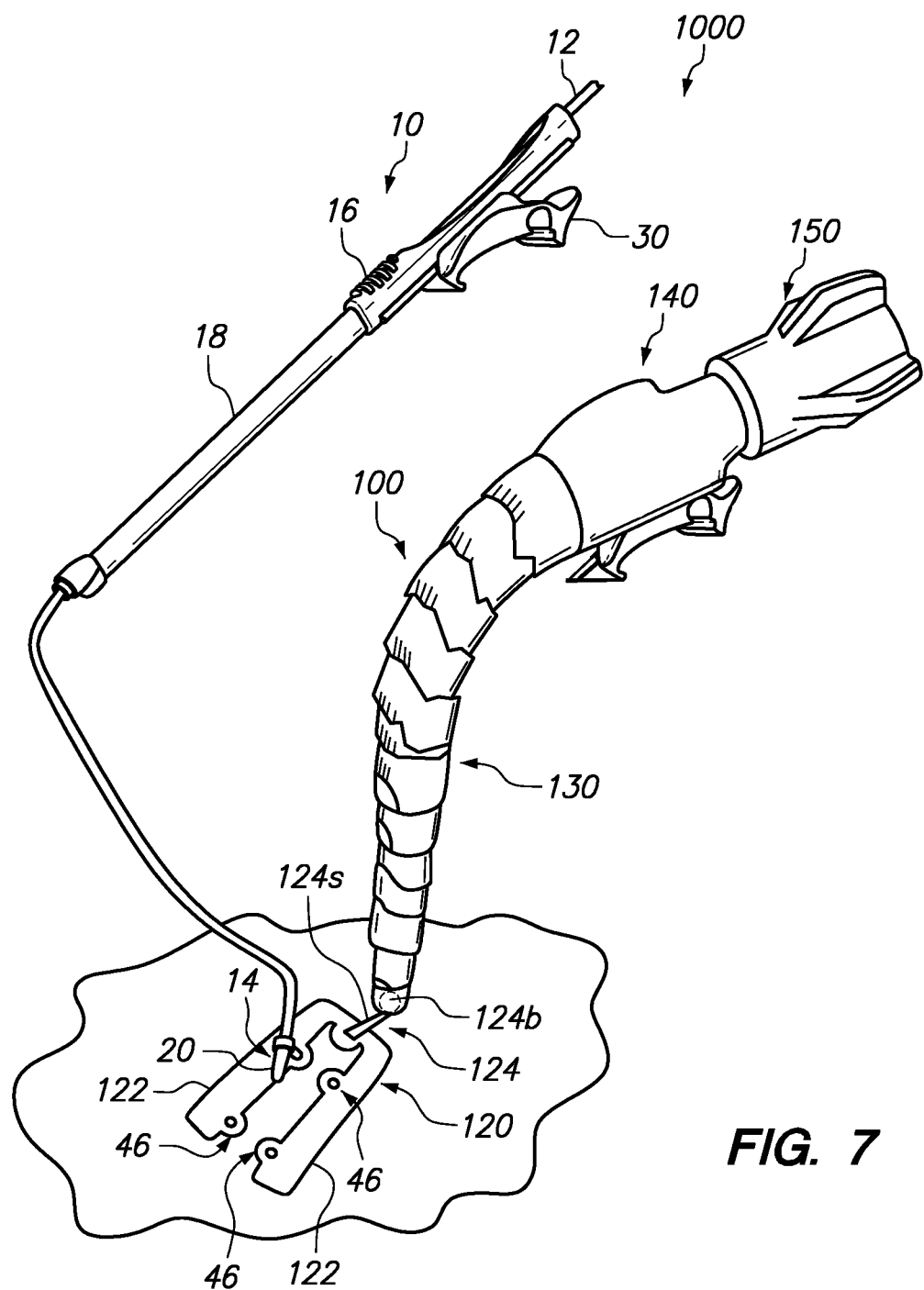

FIG. 7 shows an apparatus comprising a blower instrument 10 and an exemplary stabilizer instrument 100 with the distal tip 14 of the blower instrument having been temporarily attached to the stabilizer foot 120. Tip 14/nozzle 20 can be extended distally from the sheath 18 by a distance up to about six to about twelve inches, although this maximum distance may vary. Of course, tip 14/nozzle 20 can also be extended by distances less than the maximum extendible distance. It is noted here that the stabilizer 100 shown is only one example of a stabilizer instrument that can be used to carry out the present invention and is in no way limiting, as there are numerous other stabilizer instruments that could be substituted, as long as the foot of the stabilizer foot is configured to temporarily mate with the distal tip of the blower instrument. As such, the stabilizer foot needs to include at least one mating member 46 as described herein.

As shown, stabilizer instrument 100 is adapted to be mounted to a sternal retractor assembly for performing a mid-sternal surgical procedure on the beating heart, although the present invention is not limited to such an application, as described above. Stabilizer 100 includes an elongated shaft or arm 130 which may be rigid, or which may have a flexible, unlocked configuration and a rigid, locked configuration, as shown. In the example shown, shaft/arm 130 is a multi-jointed device which provides the flexibility needed to reach less direct surfaces of the heart from the incision opening. A connector mechanism 140 is connected to a proximal end of shaft/arm 130 and is configured to fix the stabilizer 100 to a stationary object such as a sternal retractor. The stabilizer instrument 100 may be fixed to other types of stationary objects rather than a sternal retractor. Actuator 150 is provided to change states of arm 130 between flexible and rigid, and may also be configured to fix and release connector 140 to and from a stationary object.

A stabilizer foot 120 is coupled to the distal end of shaft/arm 130 via a fitting 124. The configuration of the fitting may vary. In the example shown in FIG. 7, the fitting 124 includes a shaft 124s and a ball 124b (shown in phantom lines) that mates in a socket in the end of arm 130. Stabilizer foot 120 is adapted to contact the heart adjacent the site desired to be stabilized. Foot 120 includes at least one contact member 122 and has a pair of contact members 122 in the embodiment shown in FIG. 7. Each contact member 122 has a contact surface adapted to contact tissue to stabilize the tissue. The contact surface of each contact member 122 may be substantially planar, or slightly curved to conform to the shape of the heart, or one or more may have a non-conforming curve to establish a contact between only a portion of the contact surface of the contact member 122 and the beating heart. The shape of the contact member(s) 122 and the foot 120 may be varied depending on the clinical assessment by the surgeon, the design of the remainder of the stabilizer 100, and/or the design of other instruments to be used to complete the anastomosis Stabilizer foot 120 includes at least one mating member 46. The embodiment of FIG. 7 includes four mating members 46. Each mating member is configured and dimensioned to releasably attach to attachment member 42 of blower instrument 10. In the embodiment shown, attachment member 42 is a post and mating member 46 is a hole or socket having a diameter configured to form a friction fit with post 42. Accordingly, upon inserting post 42 into hole or socket 46, tip 14 is fixed relative to foot 120. However, a user can rotate the tip 14/nozzle 20 without breaking the connection between attachment member 42 and mating member 46 using manual force. The friction fit provides sufficient resistance to prevent tip 14/nozzle 20 from rotating relative to foot 120 during use, absent manually applied torque. Alternative types of attachment members and mating members may be substituted as already noted above. However, the temporary attachments provided by such alternative attachment members and mating members should function similarly to the embodiment described herein.

Figure 8:
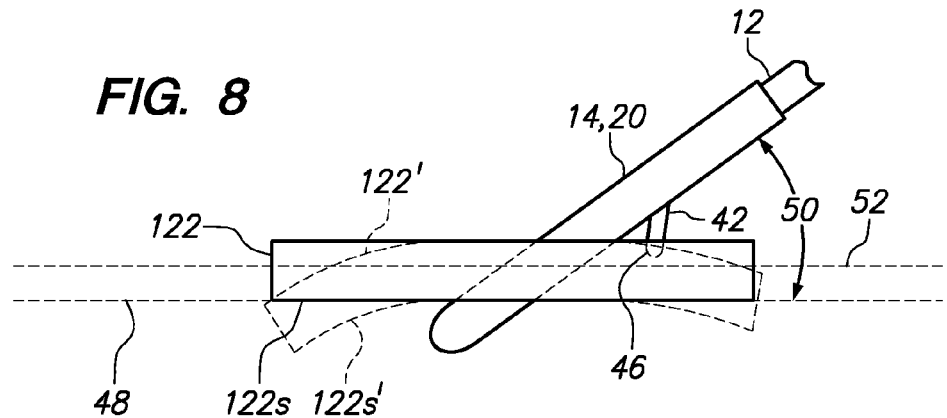

Attachment member 42 extends from distal tip 14/nozzle 20 at an angle that maintains the orientation of the distal tip 14/nozzle 20 at a predefined angle relative to the plane that the contact member 122 generally extends along, so that the distal tip is oriented non-parallel to the plane. FIG. 8 schematically illustrates this feature. The attachment member 42 and mating member 46 are oriented to the distal tip 14/nozzle 20 and to the contact member 122 or other portion of foot 120 in a configuration that maintains angulation of the distal tip 14/nozzle 20 relative to the plane 48 along which the contact surface 122s generally extends at a constant angle 50. In the example of FIG. 8, angle 50 is about seventy degrees. However, the attachment members may be oriented to as to maintain a predefined angle that is selected from a range of about fifty-five degrees to about eighty-five degrees. In any case, rotation about an axis perpendicular to the plane 48 is permitted while angle 50 is maintained. Phantom lines in FIG. 8 show an alternative embodiment of contact member 122' that has a contoured contact surface 122s' to generally follow the curvature of a heart surface. However, the contact surface 122s' is still considered to generally extend in plane 48. The longitudinal axis 52 of the contact member 120 is also considered to be parallel to the plane 48.

Further details about stabilizer instrument 100 as well as a sternal retractor that it can be mounted to (blower instrument can be mounted thereto as well, using clip 30) can be found in U.S. Pat. No. 6,758,808 which is hereby incorporated herein, in its entirety, by reference thereto.

Figure 9A:
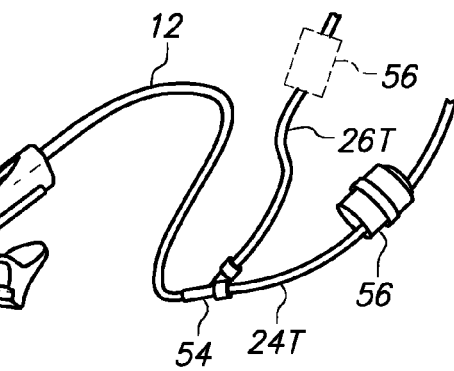
FIG. 9A illustrates one or more flow control mechanisms that may be provided with a blower instrument according to an embodiment of the present invention.
Figure 9B:
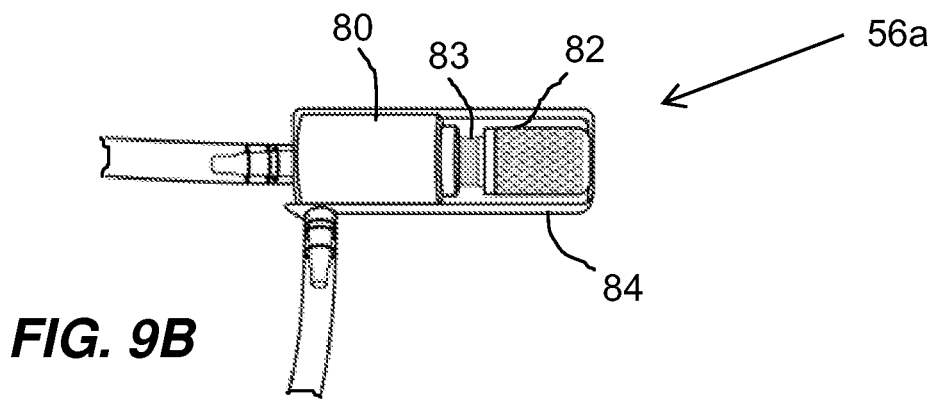
FIG. 9B illustrates an alternative flow control mechanism according to an embodiment of the present invention in an open position.
Figure 9C:
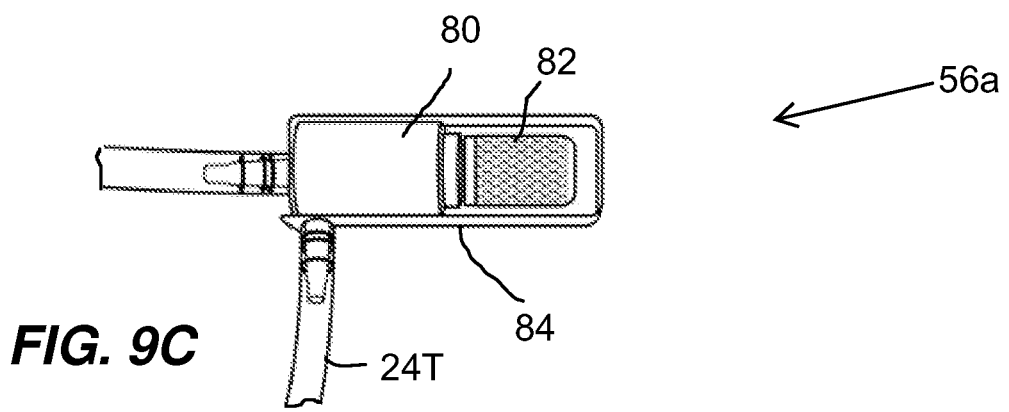
FIG. 9C illustrates the control mechanism of FIG. 9B in a closed position.

FIG. 9A illustrates a blower instrument according to the present invention wherein a flow adjustment mechanism 56 is optionally provided to control an amount/pressure of flow through one or both of lumens 24, 26. As shown, a flow adjustment mechanism 56, such as a regulator, is provided in or on tube 24T that connects, through Y-connector 54 with lumen 24 in tube 12 or 13 (FIGS. 2A-2C). Further optionally, a flow adjustment mechanism may be provided in or on tube 26T to control the flow of fluid through lumen 26. As shown, a flow adjustment mechanism is provided (in phantom lines) on tube 26T that connects, through Y-connector 54 with lumen 26 in tube 12. Various types of regulators/restriction mechanisms can be used to control the amount of flow through one or both lumens 24, 26. Further optionally, flow adjustment mechanism may be of a type described in U.S. Pat. No. 6,168,577 and may be provided in or on handle 16. FIGS. 9B and 9C illustrate a further embodiment of a flow adjustment mechanism 56A. Flow adjustment mechanism 56A has a body 80, a rotatable knob 82 with a thread 83 connected to the body 80, and a bracket 84 for limiting threaded movement in a first direction. Knob 82 has a larger diameter than thread 83 and limits movement of the knob with respect to the body 80. The threads 83 of knob 82 may be metal machine threads to provide for fine adjustment of the flow of liquid and/or gas through the flow adjustment mechanism.

Figure 10A:
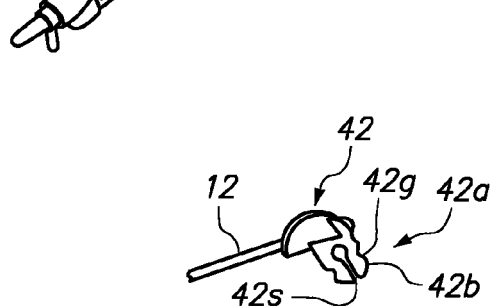
FIG. 10A shows an alternative embodiment of an attachment member provided on a blower device distal tip according to the present invention.
Figure 10B:
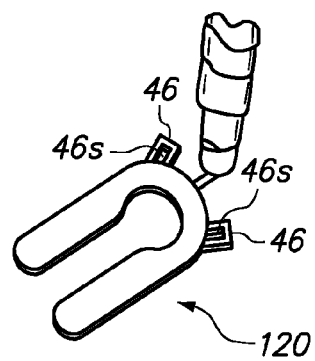

FIG. 10A shows an alternative embodiment of attachment member 42 provided on blower device distal tip 14 and FIG. 10B shows mating members 46 provided on stabilizer foot 120. In this embodiment, attachment member 42 is a slotted 42s snap that forms a living hinge, so that when inserted into slot 46s of attachment member 46, the living hinge of the attachment member allows the arms 42a to be compressed against one another to allow arms 42a to be inserted through slot 46. When distal portions 42b of arms 42a have passed through slot 46s, the living hinge elastically returns the arms 42a to their original configuration shown in FIG. 10A as the edges of slot 46s seat in grooves or notches 42g, thereby securing the attachment member 42 relative to stabilizer foot 120/attachment member 46. The operator can pull on attachment member 42 with manual force sufficient to cause arms 42a to be compressed together, thereby allowing attachment member 42 to be removed from attachment member 46/slot 46s.

FIGS. 11A-11B show another alternative embodiment of attachment member 42 provided on blower device distal tip 14 and FIG. 11C shows mating members 46 provided on stabilizer foot 120. In this embodiment, attachment member 42 includes socket 42a that is adapted to fit over ball 46b of mating member 46. Attachment member 42 may be slotted 42s or otherwise configured to allow the socket 42a to expand to receive ball 46 therein, and then to contract back to a starting configuration, so that the reduced diameter opening 42c is less than the diameter of the ball 46b and therefore prevents ball 46b from escaping from socket 42c during normal use. Socket 42a may form a friction fit with ball 46b to maintain the tip 14 in an orientation (e.g. including angle 50, as well as rotational orientation about the longitudinal axis of attachment member 46, relative to stabilizer foot 120, but to allow manual adjustment at will of the orientation by a user. Manual removal of attachment member 42 from attachment member 46 can also be accomplished by hand by a user by simply pulling the tip 14 and attachment member 42 off of the ball 46b. Mating members in this case comprise a ball 46b and post 46p.

FIG. 12 illustrates a blower instrument 10' according to another embodiment of the present invention. In this embodiment, the working end portion of instrument 10' is incorporated into a contact member 122 of the stabilizer instrument 100. The instrument 10' includes a hood 60 that extends along at least a portion of the length of the inside edge of the contact member 122, typically along all or substantially all of that length, as is the case in the example shown in FIG. 12. Hood 60 includes a slot 62 extending along the length thereof and configured to allow blower/mister spray to be emitted therethrough. FIG. 13 is an end view illustration of the contact member 22 having the hood 60 integrated therewith. Slot 62 encompasses about 90 to about 150 degrees of arc (typically about 120 degrees, as shown in FIG. 13) to allow the spray to be directed toward the surgical target area when it is located between the contact members 122.

A tube 64 having a closed distal end and at least one nozzle 20' is provided which is configured and dimensioned to slide axially within hood 60 as well as to rotate about its longitudinal axis relative to hood 60. An actuator 66 (e.g., lever arm, as shown, or other actuator that is readily manipulatable by a human user) is attached to the proximal end portion of tube 64 and is operable by a user to translate and/or rotate the tube 64. Sufficient friction exists between the tube 64 and hood 60 to maintain the tube 64 in its intended position once it has been placed there by operating actuator 66. Optionally, a friction member 68, such as an O-ring or the like, may be attached to the hood at or near the exit location of the tube 64, to establish additional friction for holding tube 64 in a desired position and orientation.

Figure 14A:
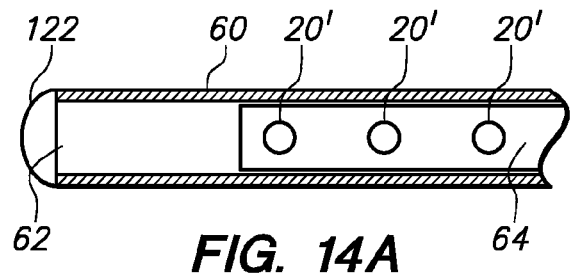
Figure 14B:
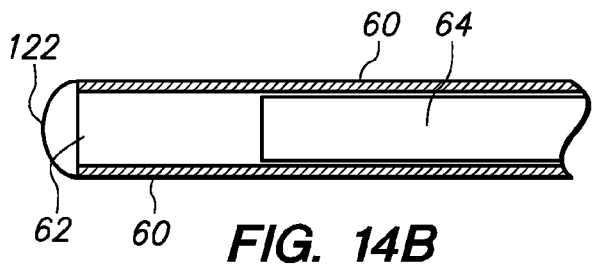

FIGS. 14A-14D illustrate partial views of blower 10' as integrated into contact member 122, from an inside-out view, i.e., as viewed in the direction indicated by arrow 1114 in FIG. 12. In FIG. 14A, tube 64 has been partially axially retracted, and has been rotated, relative to hood 60 to align nozzles 20' with slot 62 to enable spray to be directed out through nozzles 20' and slot 62 to the surgical target area located between the two contact members 122. In FIG. 14B, tube 64 has been rotated (using actuator 66) so that nozzles 20' are no longer aligned with slot 62. This effectively "turns off" the spray to the surgical target area, even if the spray continues to be delivered through nozzles 20', since the nozzles 20' are no longer pointed toward the surgical target area, and because the spray is directed into the hood 60, which mutes the spray. Optionally, the source of the spray (e.g., see 90 and 92 in FIG. 1) can also be turned off to stop the spray, whether nozzles 20' are in the orientation shown in FIG. 14A or 14B. However, actuator 66 alone is sufficient to effectively turn off the spray to the surgical target area, making it very convenient to the surgeon to turn the spray on or off simply by operating the actuator 66.

Figure 14C:
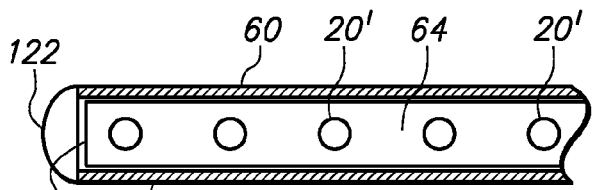
Figure 14D:
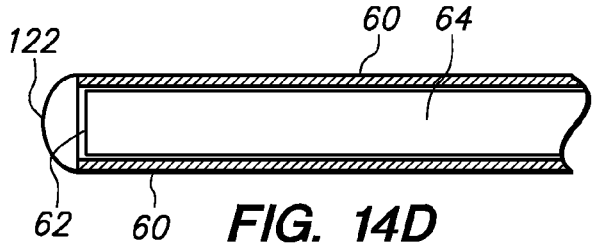

FIG. 14C illustrates the tube 64 having been again rotated to align nozzles 20' with slot 62. Additionally, actuator 66 has been slid distally relative to contact member 122 to advance tube 64 to substantially fill the full length of the space of the hood 60. In this configuration, the spray is delivered along a longer axial path and therefore a relatively larger area of the surgical target area is sprayed, compared to that shown in FIG. 14A. FIG. 14D illustrates the tube 64 having been rotated from its position in FIG. 14C to turn off the spray to the surgical target area. Tube 64 has an outside diameter of about 0.100" to about 0.150", typically about 0.12", and nozzles 20' are about 0.025" to about 0.035" in diameter at the outside surface of the tube 64, typically about 0.030". The actuator 66 may be manipulated by hand, but more often is manipulated using a pair or surgical forceps or other grasping type surgical instrument.

The angle of spray can be adjusted by rotating tube 64, as nozzles 20' may assume different angular orientations relative to slot 62 and still remain fully or partially aligned with slot 62. The axial location of the spray is adjustable by pulling the tube 64 out of the hood 60 or pushing the tube 64 further into the hood 60.

In the embodiment shown in FIG. 12, the contact members are in fluid communication with a source of suction provided by suction tube 132 that apply suction through suction ports in the contact surfaces of the contact members 122 in a known manner. Running alongside of suction tube 132 (at least near the location of attachment to the working portion 120) is tube 12 that is in fluid communication with tube 64 and provides gas and liquid to tube 64 in a manner as described previously, e.g., with regard to FIG. 1. Tube 12 may includes lumens 24 and 26 in any of the configurations described previously. Although a malleable rod 22 could be included, it is typically not needed for this embodiment.

FIG. 15 illustrates a blower instrument 10" according to another embodiment of the present invention. In this embodiment, the working end portion of instrument 10" is mounted on the crosspiece 123 of the stabilizer foot 120 via rigid post 70. Tube 12 is in fluid communication with malleable arm 72 through an opening provided through shaft 70 where the malleable arm 72 is mounted to shaft 70. Tube 12 is connected to sources of pressurized gas and liquid and can be configured in any of the manners described above. Typically, a malleable rod 22 is not included in tube 12, although tube 12 is not precluded from being so configured. Malleable arm 72 may be constructed of a double lumen plastic tube, with one lumen 724 delivering the spray and the other lumen 726 holding a malleable rod or wire 22 as illustrated in the non-limiting examples shown in the cross-sectional illustrations of FIGS. 16A and 16B. In one example, lumen 724 has an inside diameter of about 0.030" and malleable rod 22 has an outside diameter of about 0.020". Malleable rod or wire 22 may be made from copper, stainless steel, or other metal. An actuator 76 (e.g., a stopcock in the example shown in FIG. 15, or other valve mechanism that can be manipulated by a user to turn the spray on and off) is provided in post 70, in fluid communication with tube 12 and malleable arm 72/lumen 724, configured so that an operator can turn the actuator off and stop the flow of spray out of tip 14"/nozzle 20", as well as turn on the spray to allow it to be delivered out of tip 14"/nozzle 20". Malleable arm 72 can be manipulated by the used to change the direction of spray, angle of spray etc. By bending the malleable arm 72 into the desired configuration to cause tip 14"/nozzle 20" to point in a desired direction, the malleable arm retains this shape upon release of the manual force applied thereto by the operator.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention.

That which is claimed is:

1. A surgical blower instrument for delivering a fluid to clear a surgical site comprising wherein the fluid is a combination of a pressurized gas and a liquid:
   a handle;
   an elongate sleeved body extending from the handle, the elongate sleeved body housing a malleable elongate shaft;
   tubing disposed along a length of the elongate sleeved body and establishing a first elongate lumen and a second elongate lumen, wherein the first and second elongate lumens are (i) fluidically isolated from each other along at least a substantial portion of the elongate sleeved body, and (ii) combined at a distal region of the blower instrument to exit at a nozzle removably supported at a distal end of the elongate sleeved body,
   wherein the nozzle is configured for delivering the fluid to clear the surgical site and comprises a first recess formed on a first side surface of the nozzle to facilitate gripping and positioning of the nozzle; and
   wherein the nozzle and a distal end of the sleeved body are configured to permit removal and insertion of the nozzle from the distal end of the sleeved body and to permit an adjustment to a distance between the nozzle and the distal end of the sleeved body.

2. The surgical blower instrument of claim 1, wherein the nozzle further comprises a second recess formed on a second side surface of the nozzle.

3. The surgical blower instrument of claim 2, wherein the first recess comprises a generally flat surface portion.

4. The surgical blower instrument of claim 2, wherein the first and second recesses are parallel to each other and are configured to be grasped by tweezers and/or forceps.

5. The surgical blower instrument of claim 2, wherein the first recess is bounded by a proximally facing distal surface and a distally facing proximal surface for facilitating removal and insertion of the nozzle from the sleeved body.

6. The surgical blower instrument of claim 2, further comprising an attachment member extending from the nozzle and configured to be releasably attached to a mating member of a separate stabilizer instrument.

7. The surgical blower instrument of claim 6, wherein the attachment member comprises a post.

8. The surgical blower instrument of claim 7, wherein the post has a step configuration for seating and elevating the surgical blower relative to the stabilizer instrument.

9. The surgical blower instrument of claim 7, wherein the attachment member extends from the nozzle at a location in proximity to a distal end thereof through which the fluid is delivered.

10. A surgical system comprising:
a surgical blower instrument for spraying a fluid, wherein the surgical blower instrument comprises:
a handle and an elongate sleeved body extending from the handle and housing tubing within the sleeved body; and
a nozzle removably attachable to and extending from a distal end of the elongate sleeved body, wherein the nozzle is in fluid communication with a lumen established by the tubing, and wherein the nozzle is configured for spraying the fluid conveyed through the lumen, and wherein a recess is formed on a surface of the nozzle to facilitate gripping and positioning of the nozzle; and
a stabilizer instrument for stabilizing a surface of a heart, wherein the surgical blower instrument is releasably mounted to the stabilizer instrument.

11. The surgical system of claim 10, wherein the surgical blower instrument further comprises an attachment member extending from the nozzle configured to be releasably attached to the stabilizer instrument.

12. The surgical system of claim 11, wherein the attachment member comprises a post for mounting to a foot of stabilizer instrument.

13. The surgical system of claim 11, wherein the attachment member extends from the nozzle at a location adjoining the distal end through which the fluid is delivered.

14. The device surgical blower instrument of claim 1, wherein a length between the nozzle and the handle is adjustable.

15. A surgical system comprising:
a sternal retractor comprising a least one rail;
a stabilizer instrument for stabilizing a surface of a heart and reversible connectable to the sternal retractor, the stabilizer instrument comprising a foot; and
a surgical blower instrument for spraying a fluid, wherein the surgical blower instrument comprises:
a handle and an elongated sleeved body extending from the handle and housing tubing and a malleable shaft within the sleeved body, and
a nozzle removably attachable to and extending from a distal end of the elongated sleeved body, wherein the nozzle is in fluid communication with a lumen established by the tubing, and wherein the nozzle is configured for spraying the fluid conveyed through the lumen, and wherein a recess is formed on a surface of the nozzle to facilitate gripping and positioning of the nozzle; and
a clip slidably configured relative to the handle and further configured to be releasably attachable to the rail of the sternal retractor;
wherein a distal portion of the surgical blower instrument is releasably mounted to the stabilizer instrument.

16. The surgical system of claim 10, further comprising a malleable shaft extending along the length of the elongate sleeved body.

17. A method for delivering a fluid to a surgical site using the surgical blower according to claim 15; wherein the method comprises the step(s) of:
grasping the recess of the nozzle to facilitate mounting of the surgical blower instrument to a stabilizer instrument.

18. The method of claim 17, wherein the method further comprises the step of grasping the recess to position the nozzle relative to the distal end of the elongate sleeved body of the surgical blower instrument.

19. The method of claim 17, further comprising the step of rotationally adjusting the nozzle relative to the stabilizer instrument after mounting thereto.

20. The method of claim 17, further comprising the step of grasping the recess of the nozzle to facilitate detachment of the surgical blower instrument from the stabilizer instrument.

* * * * *